(12) United States Patent
Song et al.

(10) Patent No.: US 7,718,780 B2
(45) Date of Patent: May 18, 2010

(54) **PREPARATION OF MONOCLONAL ANTIBODY TO *N-MYC* DOWNSTREAM REGULATED GENE 2 AND DETERMINATION OF NDRG2 USING PROTEIN CHIP**

(75) Inventors: Eun Young Song, Seoul (KR); Jae Wha Kim, Seoul (KR); Hee Gu Lee, Daejeon (KR); Jong Seok Lim, Seoul (KR); Seung Chul Choi, Daejeon (KR); Mi Young Cho, Daejeon (KR); Kyoung Eun Baek, Daejeon (KR); Jin Sook Kim, Daejeon (KR); Jong Tae Kim, Daejeon (KR); Do Young Yoon, Seoul (KR); Dur Han Kwon, Daejeon (KR); Mi-Young Park, Daejeon (KR); Young Il Yeom, Daejeon (KR); Yong-Kyung Choe, Daejeon (KR); Young-Jun Kim, Daejeon (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 683 days.

(21) Appl. No.: 11/393,897

(22) Filed: Mar. 31, 2006

(65) Prior Publication Data

US 2007/0128194 A1    Jun. 7, 2007

(30) Foreign Application Priority Data

Dec. 6, 2005    (KR) .................... 10-2005-0118140

(51) Int. Cl.
*C12P 21/08* (2006.01)
*C07K 16/00* (2006.01)
*C12N 5/06* (2006.01)
*C12N 5/16* (2006.01)

(52) U.S. Cl. .................... 530/388.7; 435/343

(58) Field of Classification Search ............ None
See application file for complete search history.

(56) References Cited

OTHER PUBLICATIONS

Fuller et al., 2000, Preparation of Monoclonal antibodies, pp. 11.4.1-11.4.5.*
Sheehan et al., 2005, Mol. Cell. Prot. vol. 4: 346-355.*
Michaelsen et al., 2004, Scan. J. Immunol. vol. 59: 34-39.*
Accession No. NM-016250, 2008, pp. 1-5.*
Campbell, Monoclonal antibodiy Technology, 1984, pp. 1-32.*
Eriks A. Lusis et al., "Integrative Genomic Analysis Identifies *NDRG2* as a Candidate Tumor Suppressor Gene Frequently Inactivated in Clinically Aggressive Meningioma," Cancer Research Article 2005, vol. 65, No. 16, pp. 7121-7126, Aug. 15, 2005.
Seung-Chul Choi et al., "Expression and regulation of NDRG2 (N-myc downstream regulated game 2) during the differentiation of dendritic cells," Federation of European Biochemical Societies letters, pp. 413-418, Oct. 3, 2003.
Xianghu Qu et al., "Characterization and expression of three novel differentiation-related genes belong to the human *NDRG* gene family," Molecular and Cellular Biochemistry, vol. 229, pp. 35-44, 2002.
Cathy Mitchelmore et al. "NDRG2: A novel Alzheimer's disease associated protein," Neurobiology of Disease, vol. 16, pp. 48-58, Mar. 11, 2004.
Japanese Office Action (Notice of Reasons for Rejection) mailed Mar. 6, 2007 in corresponding Japanese Patent Application No. 2006-044985.
Japanese Patent Office Decision of Refusal, mailed Sep. 4, 2007 and issued in corresponding Japanese Patent Application No. 2006-044985.

* cited by examiner

*Primary Examiner*—G. R Ewoldt
*Assistant Examiner*—Amy E Juedes

(57) ABSTRACT

The present invention relates to a monoclonal antibody specific for N-myc downstream regulated gene 2 (NDRG 2) protein, a cell line producing the monoclonal antibody, a method for measuring a quantity and quality of NDRG 2 protein, and a protein chip using the same. In the present invention, NDRG 2, a cancer-related factor is specifically expressed in dendritic cells differentiated from a monocyte of human peripheral blood. Accordingly, the monoclonal antibody specific for the NDRG 2 protein, the protein chip comprising the same and the method for measuring a quantity and quality of the NDRG 2 protein by using the same can be applied to elucidate characteristics of the dendritic cell and perform a research on the NDRG 2. Therefore, the present invention may help clinically to investigate and treat intractable diseases and cancers using the dendritic cell.

2 Claims, 11 Drawing Sheets

1. Marker
2. NDRG 2 : 0.1 ug/ml
3. NDRG 2 : 0.5 ug/ml

NDRG2 (ng/ml)

| 0 | 0.05 | 0.25 | 1.25 | 6.2 |
|---|------|------|------|-----|
| 32 | 160 | 80 | 400 | 2000 |

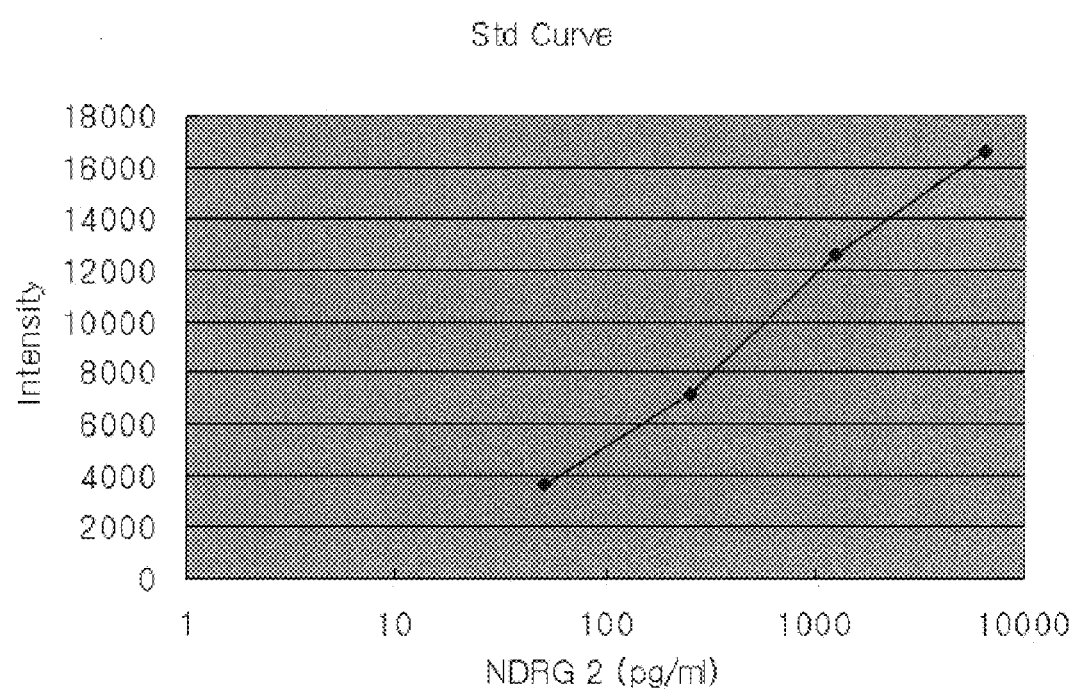

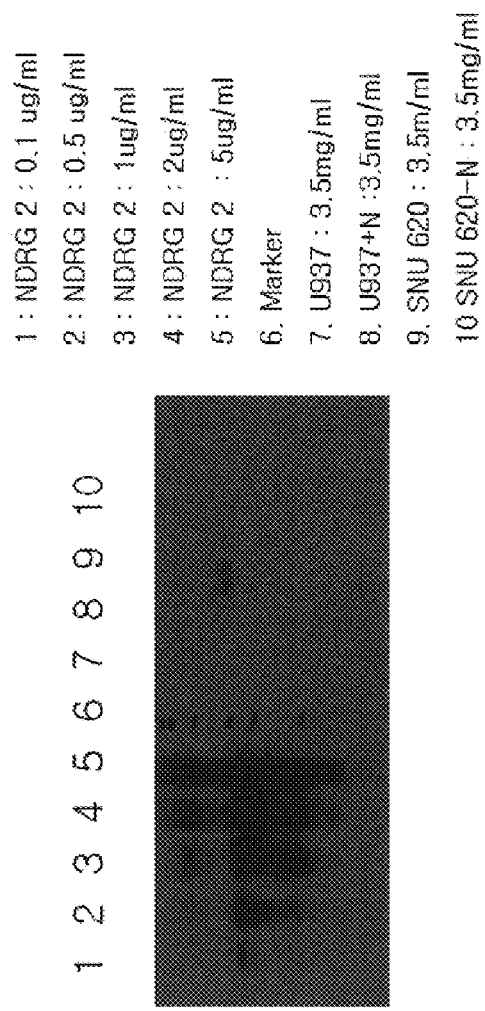

FIG. 5a

| SNU 620<br>5x | SNU 620-N<br>5x | U937<br>5x | U937+N<br>5x |
|---|---|---|---|
| SNU 620<br>25x | SNU 620-N<br>25x | U937<br>25x | U937+N<br>25x |
| SNU 620<br>125x | SNU 620-N<br>125x | U937<br>125x | U937+N<br>125x |
| O | O | O | O |
| O | O | O | O |

| 0 | 0 | N2235 125x | N2235 25x | N2235 5x |
|---|---|---|---|---|
| 0 | 0 | T2235 125x | T2235 25x | T2235 5x |
| 0 | 0 | N2327 125x | N2327 25x | N2327 5x |
| 0 | 0 | T2327 125x | T2327 25x | T2327 5x |
| 0 | 0 | N2278 125x | N2278 25x | N2278 5x |
| 0 | 0 | T2278 125x | T2278 25x | T2278 5x |

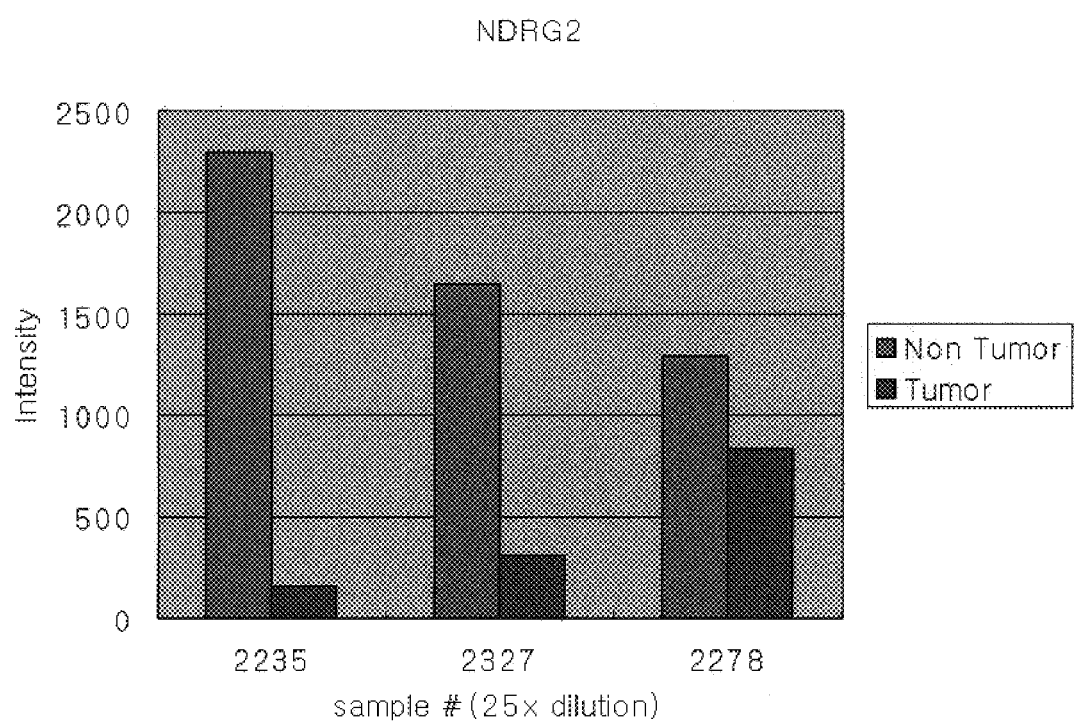

1. N2235; 2. T2235; 3. N2327;
4. T2327; 5. N2278; 6. T2278

PREPARATION OF MONOCLONAL ANTIBODY TO N-MYC DOWNSTREAM REGULATED GENE 2 AND DETERMINATION OF NDRG2 USING PROTEIN CHIP

TECHNICAL FIELD

The present invention relates to a monoclonal antibody specific for N-myc downstream regulated gene 2 (hereinafter, referred to as "NDRG 2") protein that is a candidate of tumor suppressor gene and expressed in a dendritic cell, one of human immune cells; a cell line producing the monoclonal antibody; a method for detecting NDRG 2 protein; and a protein chip using the same.

BACKGROUND ART

NDRG 2 gene is expressed in various kinds of tissue cells such as brain, muscle or kidney cells (Qu, et al., *Mol Cell Biochem.*, 229: 35-44, 2002; Kokame, et al., J. Biol. Chem., 271: 29659-29665, 1996; Ulrix, et al., FEBS Lett., 455: 23-26, 1999). It is reported that the NDRG gene may be classified to 4 different kinds. The NDRG genes have a high homology and are differentially expressed according to the development and growth of each individual. In detail, NDRG 1 gene is expressed relatively in overall tissues and cells. In contrast, NDRG 2 gene and NDRG 3 gene are expressed in brain, heart, muscle and kidney cells. NDRG 4 gene is expressed exclusively in brain and heart. Therefore, it is predicted that the NDRG genes might play different roles one another. But, there are not reports elucidating the exact functions of the genes yet.

On the other hand, dendritic cell, an antigen-presenting cell (APC) is essential to regulate a function of immune cells. The dendritic cell is a peculiar immune cell stimulating a naive T cell to induce a primary immune response. Therefore, it is actively attempted to investigate the action of dendritic cells in infectious diseases and tumor immunity. Especially in intractable diseases, genomic studies on a dendritic cell elucidating its biological function is tried to develop a vaccine applying the dendritic cell to induce a specific immunity. Recently, it is proved that the dendritic cell has a remarkable anticancer efficacy by injecting with a NK cell. Therefore, the mature dendritic cell and the NK cell may play an important role to develop a therapeutic drug using cells. In order to maximize the efficacy of the therapeutic drug, it is necessary to develop markers for this mature dendritic cell.

However, there are several problems. It is difficult to collect dendritic cells in a large scale. Further, any specific marker existing in this cell is not found, yet. Either in a clinical field, the characteristics of the dendritic cell is not fully understood. Accordingly, it is required to investigate the characteristics of the dendritic cell deeply, screen specific genes or proteins expressed in this cell and recognize their functions. Indeed, the dendritic cells may be used to treat and prevent various diseases by effective therapy.

The present inventors have already found that the NDRG 2 gene is specifically expressed in a dendritic cell differentiated from a monocyte of human peripheral blood. The NDRG 2 gene was isolated and then, introduced to a hybridoma cell line to prepare the polyclonal antibody against the NDRG 2 protein. This result has been publicly disclosed. (International Patent Application PCT/KR2004/000634; Choi, S. C. et al., *FEBS Lett.*, 553(3): 413-418, 2003)

In addition, it is reported that the NDRG 2 might be a cancer suppressor gene participating in carcinogenesis. Also, the cancinogenic cell is elucidated to reduce the gene expression of NDRG 2, and especially decrease highly in a malignant tumor. In detail, it is recognized that the expression of the NDRG 2 is reported to decrease remarkably in aggressive meningioma by conducting a genomic analysis. (Lusis, E. A. et al, *Cancer Res.*, 65: 7121-6, 2005) The mRNA amount of the NDRG 2 is also reduced in liver cancer and pancreas cancer markedly. (Hu, X. L. et al., *World J. Gastroenterol.*, 10: 3518-21, 2004). Therefore, it is expected that the NDRG 2 protein is used to treat cancers by regulating its gene expression, because reducing in carcinogenic cells notably and being focused as a cancer suppressor gene.

Nevertheless, studies on the NDRG 2 are lacked and just starting. Especially, it is required to develop a monoclonal antibody specific for the NDRG 2 protein and a method for measuring a quantity of the NDRG 2.

Since manufacturing the polyclonal antibody, the present inventors have already used it to investigate the characteristics of the dendritic cell (International Patent Application PCT/KR2004/000634; Choi, S. C. et al., *FEBS Lett.*, 553(3): 413-418, 2003). In practice, the NDRG 2 protein is measured in cells or tissues qualitatively by performing a Western blot or immuno-staining. However, there are several limitations. This immuno-staining is hardly conducted in the tissue due to a high background etc.

In order to settle above-mentioned problems, the present inventors have tried to develop a monoclonal antibody specific for the NDRG 2 protein, a cell line producing the monoclonal antibody, a method for measuring a quantity and quality of NDRG 2 protein, and a protein chip using the same that is necessary to investigate the NDRG 2 expressed in a dendritic cell and its function in a cancer cell and completed the invention successfully.

DISCLOSURE OF INVENTION

The object of the present invention is to provide a monoclonal antibody specific for NDRG 2 protein and a hybridoma cell line producing the monoclonal antibody.

The other object of the present invention is to provide a protein chip for the NDRG 2 using the monoclonal antibody and a method for measuring a quantity and quality of NDRG 2 protein using the protein chip.

BRIEF DESCRIPTION OF THE DRAWINGS

The above and other objects, features and other advantages of the present invention will be more clearly understood from the following detailed description taken in conjunction with the accompanying drawings, in which;

FIG. 4b depicts the colormetric intensity of the protein chip according to the concentration of NDRG 2 protein with a standard curve;

FIG. 4c depicts the result of Western blot using the standard NDRG 2 solution and a cell line specimen by performing a gel electrophoresis;

FIG. 5a depicts the colormetric degree of the protein chip according to the diluted concentration of each cell line;

FIG. 6b depicts the colormetric intensity of the protein chip in a 25-fold diluted sample of the liver cancer cell and normal cell;

BEST MODE FOR CARRYING OUT THE INVENTION

Figure 1:
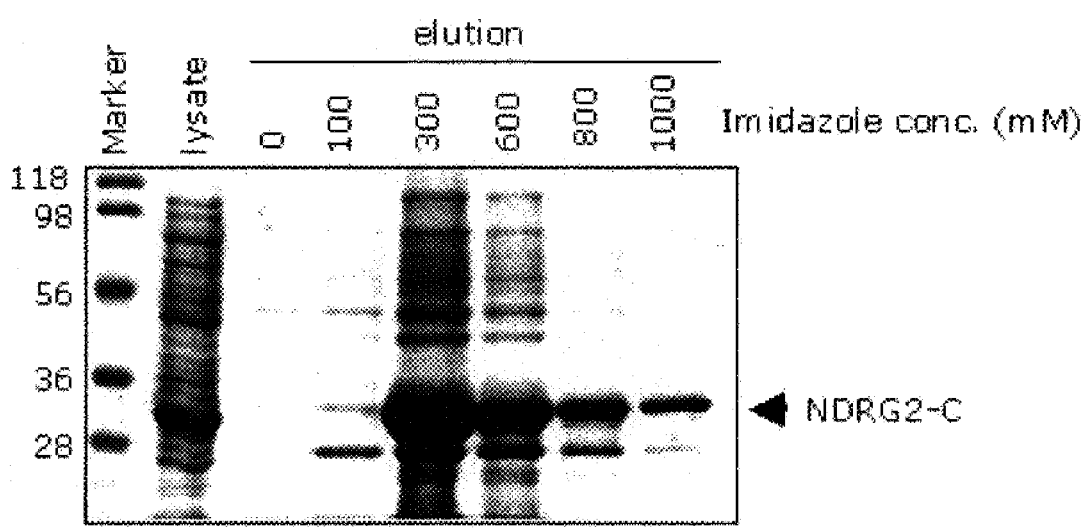
FIG. 1 depicts the expression, separation and purification of a recombinant NDRG 2 protein by performing a gel electrophoresis.

In order to achieve the above-mentioned objects, the present invention provides a monoclonal antibody specific for NDRG 2 (N-myc downstream regulated gene 2 derived from a dendritic cell.

Preferably, the dendritic cell is differentiated from a monocyte of human peripheral blood or a stem cell of umbilical blood. Preferably, the monoclonal antibody specific for NDRG 2 belongs to Subclass IgG2a.

In addition, the present invention provides a hybridoma cell line producing the monoclonal antibody and preferably, the hybridoma cell NDRG2-19C-4 (accession number: KCTC 10854 BP). A biological sample of hybridoma cell NDRG2-19C-4 was deposited with the Korean Collection for Type Culture (KCTC) on Oct. 5, 2005, as a biological deposit for Korean Patent Application No. 10-2005-0118140, which was filed on Dec. 6, 2005, and was assigned accession number: KCTC 10854 BP.

In addition, the present invention provides a method for measuring a quantity or quality of a NDRG 2 protein in a biological specimen, which comprises steps as follows: (1) preparing a reverse-phase protein micro-array integrating a biological specimen; (2) and reacting with the monoclonal antibody; (3) labeling; and (4) collecting quantitative or qualitative data.

Preferably, the monoclonal antibody used in the Step (2) is a monoclonal antibody produced from the hybridoma cell NDRG2-19C-4 (accession number: KCTC 10854 BP).

Preferably, the biological specimen is selected from a group comprising tissue, cell, whole blood, blood serum, blood plasma, saliva, cerebrospinal fluid or urine.

Preferably, the label used in the Step (3) is selected from a group comprising enzyme, fluorescent substance, ligand, luminescent or radioactive isotope.

Preferably, the data is measured in the Step (4) by using colormetric method, electrochemical method, fluorimetric method, luminometric method, particle counting method, visual assessment, or scintillation counting method.

In addition, the present invention provides a protein chip comprising a NDRG 2 protein, a monoclonal antibody specific for a NDRG 2 protein and a label.

Preferably, the monoclonal antibody used in the protein chip is a monoclonal antibody produced from the hybridoma cell NDRG2-19C-4 (accession number: KCTC 10854 BP).

The protein chip comprising the NDRG 2 protein and the monoclonal antibody specific for the NDRG 2 protein can be used to compare the expression level of NDRG 2 protein in each cell and tissue.

Hereinafter, the present invention will be described more clearly as follows.

The present inventors have already discovered a N-myc downstream regulated gene 2 (NDRG 2 gene) that is derived from the dendritic cell differentiated from a monocyte of human peripheral blood or a stem cell of umbilical blood, and manufactured a recombinant cell line transformed with this gene and a polyclonal antibody for the NDRG 2 protein, as disclosed in International Patent Application PCT/KR2004/000634.

In the present invention, the recombinant NDRG 2 protein prepared in the prior art is injected and immunized to manufacture a monoclonal antibody specific for the NDRG 2 protein. Then, a protein chip containing the monoclonal antibody is constructed and identified whether it can analyze the NDRG 2 protein quantitatively.

The monoclonal antibody is prepared by a conventional fusion method disclosed by those skilled in this art. (Kohler, et al. *European Journal of Immunology*, 6: 511-519) Generally, the hybridoma cell secreting a monoclonal antibody is prepared by fusing a cancer cell line and a proper immune cell isolated from host animal such as mice injecting antigens. This cell fusion between 2 cell groups is conducted by a conventional method already disclosed in this art, preferably by using polyethylene glycol. The resulting cell producing an antibody is cultivated and proliferated according to a typical culture procedure. Then, the cell is sub-cloned through a limited dilution to select each cell colony. After that, a hybridoma cell producing an antibody specific for a particular antigen is cultivated in vitro or in vivo in a large scale.

The myeloma cell useful for cell fusion can be selected among the myeloma cell line derived from mouse such as p3/x63-Ag8, p3-U1, NS-1, MPC-11, SP-2/0, F0, P3x63 Ag8, V653, S194 and the myeloma cell line derived from rat such as R210. In the Examples of the present invention, the myeloma cell NS-1 is used.

Precisely, in order to manufacture a monoclonal antibody that specifically recognizes human NDRG 2 protein with a high affinity, the present inventors have chosen a cDNA library of dendritic cell specifically expressing NDRG 2 gene (GenBank registration number: NM_016250) as a template and oligonucleotides of SEQ ID NO: 1 and SEQ ID NO: 2 as a primer. The NDRG 2 gene is amplified by performing a RT-PCR during 35 cycles (95° C. 1 minute, 57° C. 1 minute, 72° C. 1 minute) to obtain 627 bp fragments. Then, the resulting fragment is cloned into pEZ vector and sequenced. As a result, this gene is identified to correspond to the NDRG 2 gene (See Sequence list).

After that, the NDRG 2 gene cloned into the pEZ vector is digested with restriction enzymes Xho I and BamHI, ligated to an *E. coli* expression vector pET28 and transformed to *E. coli* BL 21 so as to produce the recombinant NDRG 2 protein composed of 207 amino acids.

The recombinant protein is utilized to immunize experimental mice. Then, spleen cells are collected from the mice and fused with a myeloma cell. After that, a hybridoma cell line specifically binding for the NDRG 2 antigen is selected. The hybridoma cell line producing a monoclonal antibody is named as NDRG2-19C-4, and deposited with the International Deposit Organization, Korean Collection for Type Cultures (KCTC) in Oct. 5, 2005 (accession number: KCTC 10854BP).

This cell clone is examined to identify a subclass type of antibody and judged as IgG2a. and has a high specificity for the NDRG 2 protein. The monoclonal antibody specific for the NDRG 2 protein is analyzed by performing a Western blotting etc. so that it is identified to have a high specificity for the NDRG 2 antigen.

In order to choose a mono-clone selectively recognizing the NDRG 2 protein, conventional methods are conducted by using a specific antibody. Preferably, the method can be selected among radioactive immunoassay (RIA), enzyme-linked immunosorbent assay (ELISA), Western blotting and FACS analysis and the like and especially in a tissue, selected from immuno-histochemistry and ELISPOT. In practice, when a biological sample is cell lysate or blood, the clone is analyzed quantitatively by using a ELISA. When it is tissue, the clone is examined by using an immuno-histochemical method. When it is cell, the clone is analyzed by using an ELISPOT or FACS analysis. Especially in the NDRG 2 protein, it is preferred to perform radioactive immunoassay (RIA), enzyme-linked immunosorbent assay (ELISA), and Western blotting after cell lysis, because the NDRG 2 is not secreted. If performing a Western blot or immuno-histochemical method in tissue, it is difficult to analyze quantitatively. If conducting a ELISA, it is disadvantageous to need too much sample for only one test.

The monoclonal antibody produced from the hybridoma cell can be used in an crude state even if not purified. Also, it can be isolated in a high purity by performing a conventional method. Preferably, dialysis, salt precipitation, ion exchange chromatography, affinity chromatography, exclusion chromatography and the like can be conducted for this purpose.

In the present invention, the NDRG 2 protein is measured by using a newly-conceptual protein chip that is treated with the NDRG 2 protein and a biological sample together. In contrast to an antibody chip that reacts a sample after integrating a general antibody, the protein chip of the present invention is an reverse-phase protein micro-array integrating a sample directly. There are a lot of advantages. This protein chip has a higher stability than the antibody chip and reacts several kinds of antibodies coincidently after integrating a sample directly. When integrating, a number of slides can be prepared even with a small amount (nl) of sample so that repeated tests, time-interval tests and several analyses of substance can be accomplished simultaneously. Further, only several cells of sample are needed on one slide.

In the description of the present invention, "biological sample" includes tissue, cell, whole blood, serum, blood plasma, saliva, cerebrospinal fluid, urine and the like. The biological sample can be reacted with the antibody or other antibodies having a specificity of the same epitope in order to measure the expression level of NDRG 2 protein regardless of the manipulation.

In the description of the present invention, "antigen-antibody complex" means a conjugate of the NDRG 2 protein and the monoclonal antibody that is reacted to identify whether the NDRG 2 is expressed within a biological sample or not. The formation of antigen-antibody complex is detected by using a method selected from a group comprising colorimetric method, electrochemical method, fluorimetric method, luminometric method, particle counting method, visual assessment, and scintillation counting method. However, it is natural that the method is not limited.

In the description of the present invention, "detection" aims at detecting a antigen-antibody complex. In this process, various labels are used and can be selected from a group comprising enzyme, fluorescent substance, ligand, luminescent substance or micro-particle and radioactive isotope. However, it is natural that the method is not limited. Preferably, the enzyme for this label use can be selected among acetylcholinesterase, alkaline phosphatase, β-D-galactosidase, horseradish peroxidase, β-lactamase and the like. Preferably, the fluorescent substance for this label use can be selected among fluorescein, $Eu^{3+}$, $Eu^{3+}$ chelate or cryptate and the like. Preferably, the ligand for this label use can be selected among acridium ester, isoluminol derivative and the like. Preferably, the micro-particle for this label use can be selected among gold colloid, colored latex and the like. Preferably, the radioactive isotope for this label use can be selected among $^{57}Co$, $^{3}H$, $^{125}I$, $^{125}$ I-Bonton Hunter's reagent and the like.

Practically in the examples of the present invention, the amount of NDRG 2 protein is measured by using the monoclonal antibody on the protein chip. The diluted solution of the recombinant NDRG 2 protein and tissue and cell lysate are coated onto a membrane-treated slide with a protein array and reacted with the antibody prepared above. After amplifying the reaction, the resultant is colored by using DAB (3,3'-diaminobenzidine tetrahydrochlorate), scanned with a scanner and measured for colormetric intensities by using GenePix program (Axon, USA). Then, the NDRG 2 protein in the sample is calculated with a standard test curve. By this analytic procedure, the concentration of the NDRG 2 can be measured to 50 pg/ml of level.

EXAMPLES

Practical and presently preferred embodiments of the present invention are illustrated as shown in the following Examples.

However, it will be appreciated that those skilled in the art, on consideration of this disclosure, may make modifications and improvements within the spirit and scope of the present invention.

Example 1

Preparation of Recombinant Human NDRG 2 Protein

The cDNA library of a dendritic cell expressing NDRG 2 gene (GenBank registration number: NM_016250) specifically as a template and oligonucleotides of SEQ ID NO: 1 and SEQ ID NO: 2 as a primer were adopted. The NDRG 2 gene was amplified by performing a RT-PCR during 35 cycles (95° C. 1 minute, 57° C. 1 minute, 72° C. 1 minute) to obtain 627 bp fragments. Then, the resulting fragment was cloned into pEZ vector (RNA, Korea) and sequenced. As a result, this gene is identified to correspond to the NDRG 2 gene (See Sequence list).

```
SEQ ID NO: 1:      5'-AAGGTCTTGTCCTCATCAAC-3'

SEQ ID NO: 2:      3'-TCAACAGGAGACCTCCAT-5'
```

After that, the NDRG 2 gene cloned into the pEZ vector was digested with restriction enzymes Xho I and BamHI, ligated to an *E. coli* expression vector pET28 (Novagen, Medison, Wis., USA) and transformed to *E. coli* BL 21 (Novagen, Medison, Wis., USA) so as to produce the recombinant NDRG 2 protein composed of 207 amino acids.

FIG. 1 depicts the expression, separation and purification of the recombinant NDRG 2 protein by performing a gel electrophoresis. The recombinant NDRG 2 protein was expressed in *E. coli* and passed through a Ni-NTA column. Then, the NDRG 2 protein attached onto Ni-resins was separated by changing the concentration of imidazole. In 300~1, 000 mM of imidazole concentration, the recombinant NDRG 2 protein was eluted and purified.

Example 2

Production of Hybridoma Cell Line and Monoclonal Antibody for Recombinant Human NDRG 2 Protein (1) Immunization of Antigen in Mice In order to obtain immunized mice necessary to develop a hybridoma cell line, 50 μg of recombinant NDRG 2 fusion protein prepared in the Example 1 was blended with the same volume of immune adjuvant (MPL+TDM adjuvant)(Sigma, USA) and heated in boiling water for 30 minutes at 40 to 45° C. Then, the resulting protein was injected into a peritoneal cavity of 4~6 weeked Balb/c mouse. After 2 weeks, 25 μg of the recombinant NDRG 2 fusion protein was blended with the same volume of immune adjuvant (MPL+TDM adjuvant) (Sigma, USA) and injected into the mouse peritoneal cavity again for booster. After 4~5 days, a small volume of blood was collected from an ocular vein of mouse to measure a titer. Finally, the NDRG 2 protein mixed with the immune adjuvant was re-injected into the peritoneal cavity once more before 3 days of cell fusion.

2. Preparation of Hybridoma by Cell Fusion

In order to perform a cell fusion necessary to prepare a hybridoma cell, the immunogen prepared in the Example 2, Step 1 was injected so as to collect $10^7$ of spleen cells and $10^6$ of myeloma cell NS-1 in a 50 ml test tube. For cell fusion, NS-1 cell was used as a parent cell. This parent cell was maintained in approximately $5\times10^6$ cells/ml of the maximal density by using a DMEM medium containing 10% FBS.

The mouse immunized in the Example 2, Step 1 was anesthetized with ether. Then, a spleen placed in the left was taken out of the body and homogenized under a mesh to make a suspension. The resulting spleen cells were centrifuged in a 15 ml centrifuge tube. This procedure was repeated twice to wash out the spleen cells sufficiently. 10 ml of spleen cells and 10 ml of NS-1 cells were re-suspended and counted respectively. The spleen cells and the NS-1 cells were blended in 10:1 ratio with a 50 ml centrifuge tube, centrifuged again and precipitated. The resulting precipitate was suspended by tapping with the fingers and maintained at 37° C. for a minute. Then, 1 ml of fusogen, 45% polyethylene glycol (PEG) included Han's buffer (HBSS) was dropped for a minute and slightly stirred again for a minute.

After that, 9 ml of culture medium (DMEM) was added for a minute and stirred with adding DMEM media slowly until reaching 30 ml. The resulting suspension was centrifuged again to collect cell precipitate. The precipitate was re-suspended in approximately 1 to $2\times10^5$ cells/ml of density by using a selective medium (HAT), poured by 0.2 ml into a 96-well microtiter plate and cultivated at 37° C. with a $CO_2$ incubator.

3. Selection of Hybridoma Cell Producing Monoclonal Antibody

In order to select a hybridoma cell specifically binding NDRG 2 antigen, the cell groups fused in the Example 2, Step 2 were screened by performing an ELISA using a his tag and his-NDRG 2 antigen composed of a his tag and the recombinant NDRG 2 protein prepared in the Example 1.

In detail, the his tag or the his-NDRG 2 antigen were added into each well of microtiter plate by 50 μl (2 μg/ml), attached onto the plate and washed out to discard free antigens. Then, hybridoma cell included in a culture medium was added to each well by 50 μl, reacted for an hour, and washed completely by using phosphate buffer—Tween 20 (PBST) to remove the culture media. After that, goat anti-mouse IgG-HRP (horseradish peroxidase) (Sigma, USA) was added, reacted at room temperature for an hour and washed sufficiently by using PBST solution. Then, a substrate solution of peroxidae was added and reacted to measure an absorbance at 490 nm.

As a result, hybridoma cell lines secreting antibodies highly specifically binding for the NDRG 2 antigen were selected. This procedure was repeated several times so as to choose a hybridoma cell line specific for the NDRG 2 antigen exclusively. By conducting a limited dilution, a hybridoma cell line producing a monoclonal antibody was selected and finally, named as NDRG2-19C-4. The hybridoma cell line NDRG2-19C-4 is deposited with the International Deposit Organization, Korean Collection for Type Cultures (KCTC) in Oct. 5, 2005 (accession number: KCTC 10854BP).

This cell clone was also cloned and stored under a freezer. The cell supernatant was examined to measure a titer and identify a subclass type of antibody. The clone NDRG2-19C-4 is judged as IgG2a and has a high specificity for the NDRG 2 protein.

4. Mass Production of Monoclonal Antibody

In order to produce a monoclonal antibody in a large scale from the hybridoma NDRG2-19C-4 prepared in the Example 2, Step 3, 0.5 ml of incomplete Freund adjuvant) (Sigma, USA) was injected into a peritoneal cavity of Balb/c mouse. After 1 week, each hybridoma cell was injected by $2\times10^6$ cells into the peritoneal cavity of the mouse. Then, the experimental mouse swollen in the peritoneal cavity was syringed to collect a peritoneal fluid. The fluid containing the hybridoma cell in a high concentration was centrifuged at 10,000 rpm to remove cell remnant. The resulting supernatant was separated and purified by using a affinity column (Protein A&G agarose column) while partially stored at −70° C.

5. Identification of Antibody Specificity for NDRG 2 Protein by Western Blot

Figure 2:
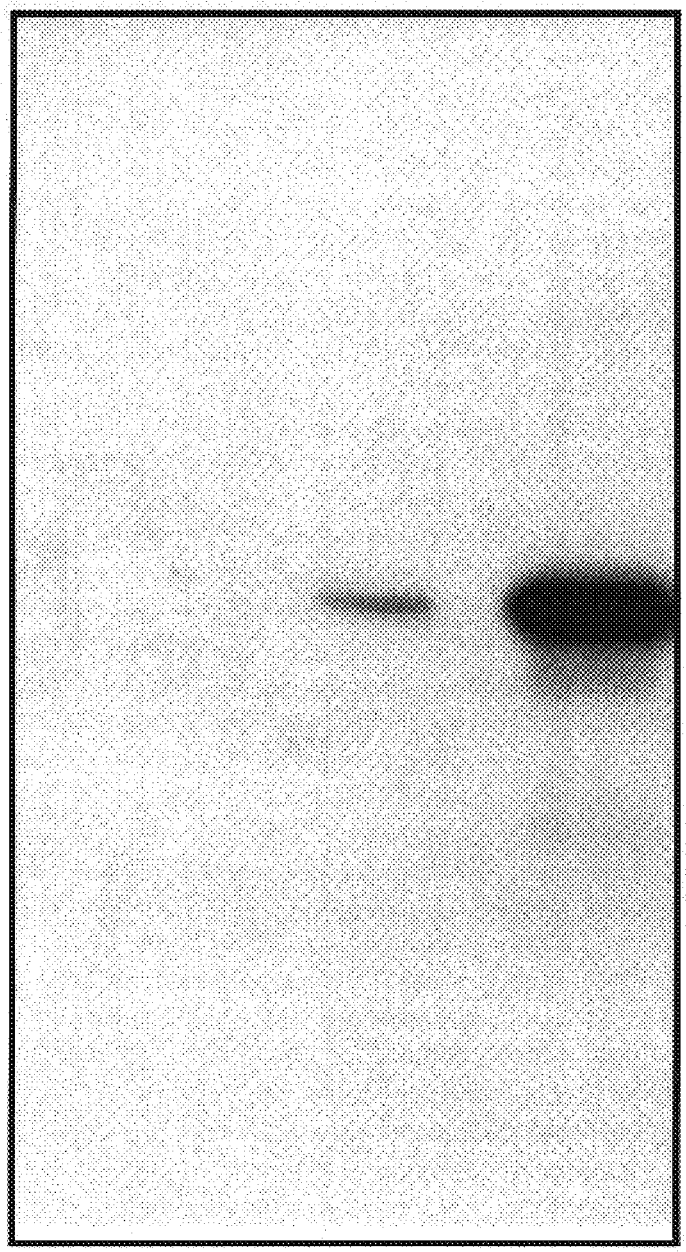
FIG. 2 depicts the reactivity of a NDRG 2 monoclonal antibody for the recombinant NDRG 2 protein by performing a western blot.

The specific reactivity of antibody for the NDRG 2 protein was examined by performing a SDS-polyacrylamide gel electrophoresis and Western blotting as illustrated in FIG. 2. 0.1 μg/ml and 0.5 μg/ml of the NDRG 2 protein were run on a SDS-polyacrylamide gel for electrophoresis, transferred onto a membrane and reacted with the monoclonal antibody prepared in the Step 4. As a result, it is observed that the NDRG 2 protein is placed at a particular band.

Example 3

Preparation of Protein Chip for NDRG 2 Protein and Measurement of NDRG 2 Protein 1. Preparation of Protein Chip In order to manufacture a protein chip spotting a standard solution of the recombinant NDRG 2 protein and a sample, the recombinant protein and a sample were diluted by using T-per tissue extraction solution respectively. For the experimental sample, a cell line, tissue lysate and serum were utilized. Each sample was spotted on a slide coated with nitrocellulose membrane (S&S, FAST slide) by using a protein arrayer (Proteagen Corporation, Korea). In this process, the standard solution of NDRG 2 protein is used to obtain a standard curve.

2. Antigen-antibody reaction

The protein chip spotting the recombinant NDRG 2 and sample prepared in the Example 3, Step 1 and a sample were washed by using PBST buffer and blocked with BSA solution. The resulting chip was colored by using Dakocytomation CAS (Catalyzed Signal Amplication System, code, K1500) kit as recommended in company manuals. The procedure was described as follows:

(1) treating hydrogen peroxide solution and after 5 minutes, washing;
(2) treating a protein block solution and placing for 5 minutes;
(3) treating a NDRG 2 antibody, reacting for an hour and washing 3 times by using a washing buffer;
(4) treating a biotin-linked antibody, reacting for an hour and washing 3 times by using a washing buffer;
(5) treating a streptavidin-biotin complex, reacting for 15 minutes and washing 3 times by using a washing buffer;
(6) treating an amplification buffer, reacting for 15 minutes and washing 3 times by using a washing buffer;
(7) treating a streptavidin-peroxidase solution, reacting for 15 minutes and washing 3 times by using a washing buffer;
(8) treating DAB (3,3'-diaminobenzidine tetrahydrochlorate) substrate and being colored;
(9) stopping the coloring reaction.

Figure 3:
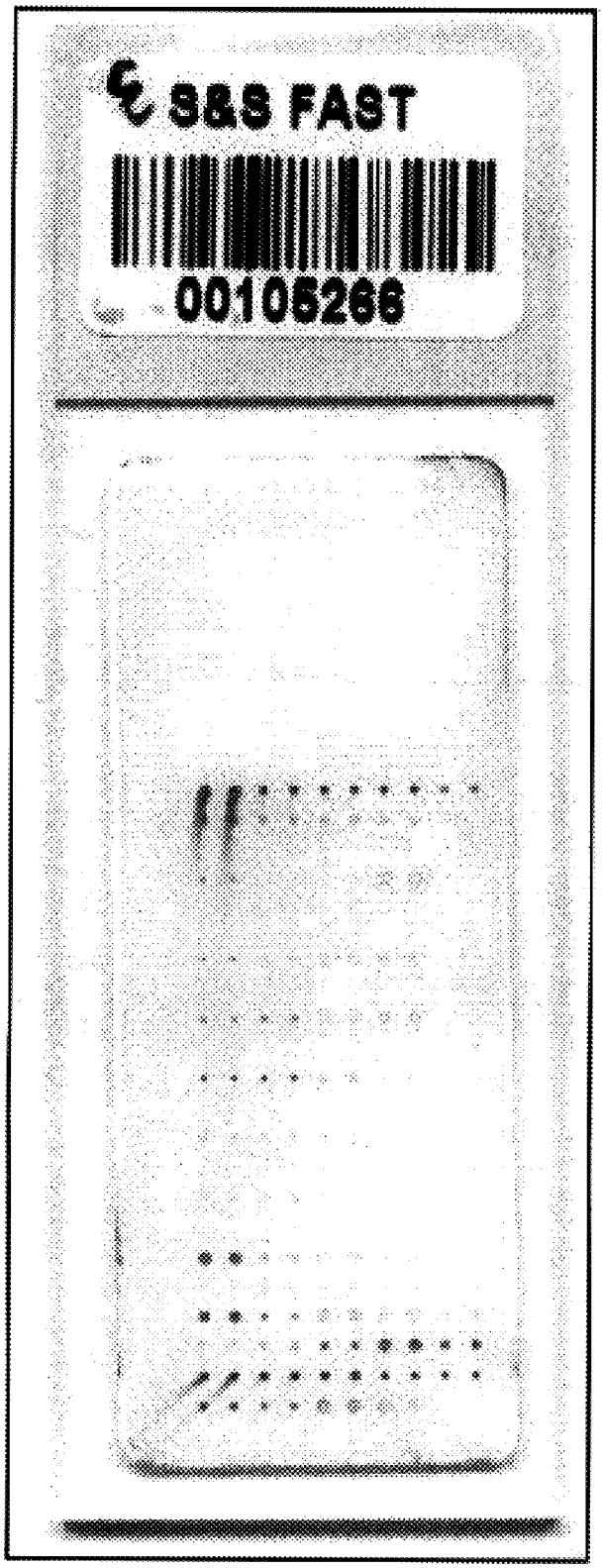
FIG. 3 depicts the colormetric observation of a protein chip treated with the NDRG protein and a specimen after reacting the NDRG 2 monoclonal antibody.

FIG. 3 depicts the colorimetric observation of the protein chip slide after completing the reaction.

Example 4

Quantitative Measurement of NDRG 2 Protein with Protein Chip

1. Preparation of Standard Curve of NDRG 2 Protein

By using a colormetric intensity of each spot of the NDRG 2 standard solution, a test curve was made.

Above all, the standard solution was prepared in 0, 0,05, 0,25, 1.25, 6.2, 32, 160, 80, 400 and 2,000 ng/ml of NDGR 2 and spotted in a duplicate onto a slide (S&S, FAST slide) respectively. After being colored as described in the Example 3, Step 2, the resulting slide was dried at room temperature and scanned with a scanner (HPscanjet 5470, USA). The pile scanned above was examined to measure a colormetric intensity at each spot by using GenePix program (Axon, USA).

Figure 4A:
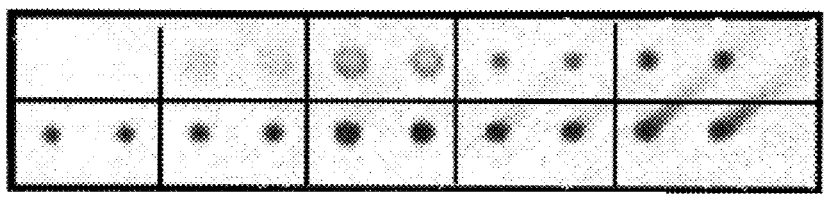
FIG. 4a depicts the colormetric degree of the protein chip according to the concentration of NDRG 2 protein in a standard solution.

FIG. 4a depicts the colorimetric degree of the protein chip according to the concentration of the NDRG 2 standard solution. The upper portion is a colored protein chip and the lower illustrates the concentration of standard sample at a relevant position of the protein chip. FIG. 4b depicts the colorimetric intensity according to the concentration of NDRG protein with a standard curve. The sensitivity is determined at less than 50 pg/ml. FIG. 4c depicts the result of Western blot using the standard NDRG 2 solution. The sensitivity is determined at approximately 100 ng/ml.

2. Measurement of NDRG 2 Concentration in Cell Line

For a cell sample, SNU 620 cell line highly expressing a NDRG 2 (acquired from Korea Cell Line Bank, Seoul National University); SNU 620-N cell line suppressing the expression of NDRG 2 gene by using Retro virus and NDRG2 siRNA; U937 cell line deficient in the expression of NDRG2 gene (ACTT, USA); and U937+N cell line over-expressing NDRG 2 gene that is cloned into pcDNA3.1 vector and transfected with U937 cell line by electro-poration were adopted. The protein concentration of each cell lysate was fixed at 1 mg/ml. Then, the cell lysate was diluted to 5-, 25- and 125-fold by using T-per tissue extraction solution and spotted in a duplicate onto a slide coated with cellulose membrane (S&S, FAST slide) respectively as described in the Example 4, Step 1. By the same procedure preparing the standard curve, each spot of sample was colored and the colormetric intensity was measured by using GenePix program (Axon, USA). Then, the concentration of NDRG 2 protein in each sample was calculated with a standard test curve.

Figure 5B:
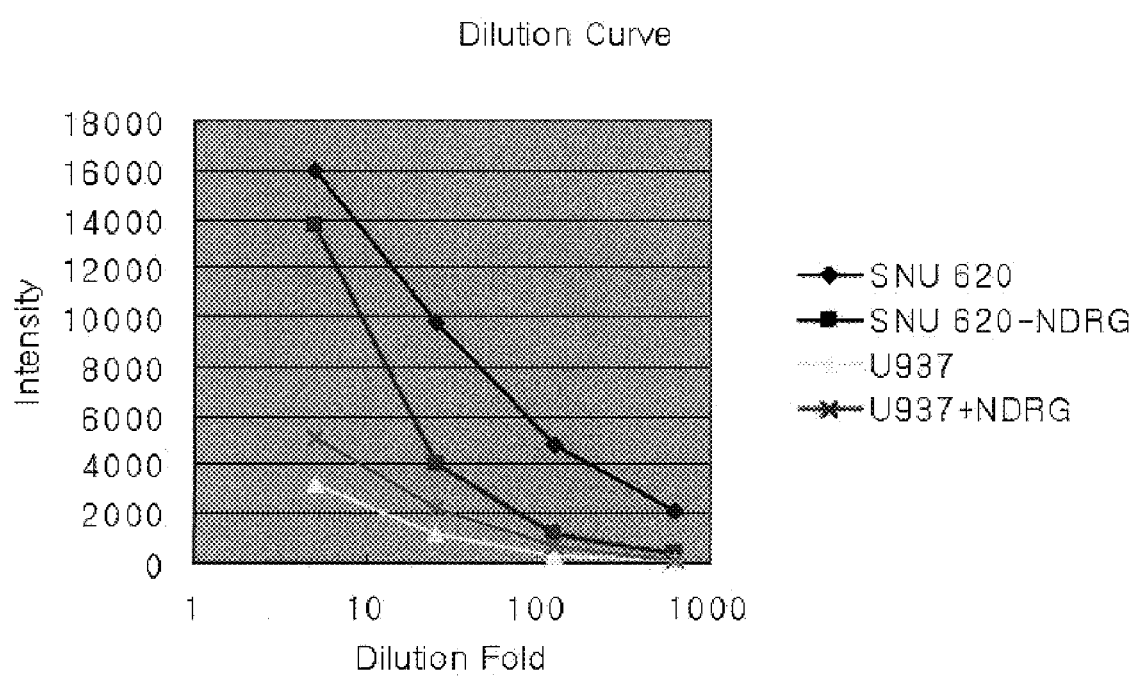
FIG. 5b depicts the colormetric intensity of the protein chip according to the diluted concentration of each cell line.

FIG. 5a depicts the colorimetric degree of the protein chip according to the diluted concentration of each cell line. The upper portion is a colored protein chip and the lower table illustrates the kind of cell lines and degree of dilution at a relevant position of the protein chip. FIG. 5b depicts the colorimetric intensity of the protein chip according to the diluted concentration of each cell line. FIG. 4c depicts the result of Western blot using the protein chip by performing a gel electrophoresis. As described in the result of Western blot, SNU 620 cell line was measured with the protein chip to produce NDGR 2 protein in a large amount. In contrast, SNU 620-N cell line suppressing the expression of NDRG 2 was observed to produce NDGR 2 protein in a small amount. In U937 cell line, NDRG2 protein was seldom detected and in U937+N cell line transformed with NDRG 2 gene, NDRG 2 was measured.

Table 1 illustrate the comparison of NDRG 2 concentration within each cell line according to the standard curve of NDRG 2 by using the protein chip to that of Western blot.

TABLE 1

| Sensitivity | | protein chip less than 50 pg/ml | Western blot 100 ng/ml |
| --- | --- | --- | --- |
| NDRG 2 concentration (ng/mg) | SNU 620 | 8.12 | 15 |
| | SNU-620 – N | 2.6 | 3 |
| | U937 | 0.00 | 0 |
| | U937 + N | 0.2 | 0.3 |

In 1 mg/ml of cell lysate, NDRG 2 protein can react although diluted to 125-fold. When considering the sample amount spotted to calculate the number of cells, it is concluded that the NDRG 2 concentration may be measured with several~several tens of cells per spot. By performing a qualitative Western blot, the similar result was also obtained so as to measure a pg/ml level of concentration.

3. Measurement of NDRG 2 in Liver Cancer Tissue

For a tissue sample, 3 patients suffering from liver cancer (NO. 2235, 2327, 2278 patients) and normal persons were operated to extract liver cancer cell and tissue and normal liver tissue respectively and dissolved. The total amount of proteins was adjusted to 1 mg/ml, then diluted in a duplicate by 5-folds to 5, 25 and 125-fold as described in the Example 4, Step 2 and spotted onto a slide. The normal cells are named as N2235, N2327 and N2278 and the liver cancer cells, as T2235, T2327 and T2278 respectively. Each spot of sample was colored as described in the Example 4, Step 3 and the colormetric intensity was measured by using GenePix program (Axon, USA). Then, the concentration of NDRG 2 protein in each sample was calculated with a standard test curve.

Figure 6A:
FIG. 6a depicts the colorimetric observation of the protein chip in each liver cancer cell and normal cell.
Figure 6C:
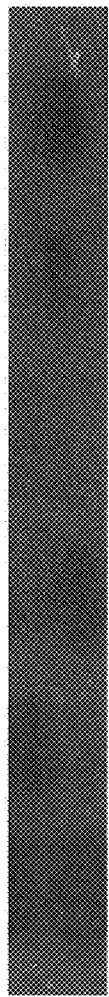
FIG. 6c depicts the result of Western blot using the liver cancer cell and normal cell by performing a gel electrophoresis.

FIG. 6a depicts the colormetric observation of the protein chip in each liver cancer cell and normal cell. The upper portion is a colored protein chip and the lower table illustrates the kind of cells and degree of dilution at a relevant position of the protein chip. Even in the 125-fold diluted sample, the NDRG 2 protein can be detected as described in the Example 4, Step 3. FIG. 6b depicts the colormetric intensity of the protein chip in each 25-fold diluted sample. FIG. 6c depicts the result of Western blot. In FIG. 6c, lane 1 is N2235, lane 2 T2235, lane 3 N2327, lane 4 T2327, lane 5 N2278, and lane 6 T2278.

As a consequence, it is observed that the NDRG 2 is less expressed in the liver cancer tissue than in the normal liver cancer tissue when using the Western blot and the protein chip. This result is similar to that of RT-PCR and the Western blot and the protein chip has a similar tendency of the expression.

Table 2 illustrates the NDRG 2 concentration within each tissue according to the standard curve of NDRG 2 by reacting each liver tissue onto the protein chip.

As illustrated in Table 2, it is estimated that the NDRG 2 concentration within the liver cancer tissue is remarkably low, compared to that in the normal liver tissue. Therefore, it is confirmed that the comparison of the NDRG 2 concentrations in the liver cancer tissue and the normal liver tissue can be applied to diagnose a liver cancer efficiently.

TABLE 2

|  |  | Normal liver tissue | Liver cancer tissue |
|---|---|---|---|
| NDRG 2 concentration (ng/mg) | #2235 | 878.3 | 28.1 |
|  | #2327 | 658.7 | 58.0 |
|  | #2278 | 111.9 | 70.0 |

4. Measurement of NDRG 2 in Serum of Liver Cancer Patient 3 patients suffering from liver cancer (NO. 2235, 2327, 2278 patients) and 3 normal persons were operated to collect serum samples respectively, diluted by 2-folds and spotted in a duplicate onto a slide. As a consequence, it is observed that the NDRG 2 protein is not expressed in both sera of normal and liver cancer. This result is identical to that of immuno-dot blotting.

INDUSTRIAL APPLICABILITY

As illustrated and confirmed above, the monoclonal antibody specific for NDRG 2 protein and the protein chip of the present invention can be used to measure the amount of NDRG 2 protein within a biological sample and further to elucidate characteristics of the dendritic cell and perform a research on NDRG 2-related carcinogenesis. The present invention may be applied to develop therapeutic drugs using the dendritic cell and diagnose a cancer.

In addition, the present invention can be used in basic researches because a number of slides for test are manufactured simultaneously. This is convenient and applicable to investigate cell-cell networking and diagnose rare samples difficult to obtain the same kind.

Those skilled in the art will appreciate that the conceptions and specific embodiments disclosed in the foregoing description may be readily utilized as a basis for modifying or designing other embodiments for carrying out the same purposes of the present invention.

Those skilled in the art will also appreciate that such equivalent embodiments do not depart from the spirit and scope of the invention as set forth in the appended claims.

The invention claimed is:

1. A monoclonal antibody specific for human NDRG 2 (N-myc downstream regulated gene 2) protein, wherein
   the monoclonal antibody is produced by a hybridoma cell line NDRG2-19C-4 (accession number: KCTC 10854 BP), and
   NDRG 2 is derived from a dendritic cell.

2. A hybridoma cell line producing a monoclonal antibody specific for human NDRG 2 protein, wherein
   the hybridoma cell line is NDRG2-19C-4 (accession number: KCTC 10854 BP).

* * * * *

SEQUENCE LISTING

```
<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: primer

<400> SEQUENCE: 1
aaggtcttgt cctcatcaac                                          20

<210> SEQ ID NO 2
<211> LENGTH: 18
<212> TYPE: DNA
<213> ORGANISM: Artificial Sequence
<220> FEATURE:
<223> OTHER INFORMATION: primer

<400> SEQUENCE: 2
tcaacaggag acctccat                                            18
```